United States Patent
Creaturo

(10) Patent No.: US 11,058,606 B2
(45) Date of Patent: *Jul. 13, 2021

(54) METHODS AND APPARATUSES FOR DELIVERING MEDICAMENTS TO INTRAVENOUS FLUID

(71) Applicant: Parenteral Technologies, LLC, Siesta Key, FL (US)

(72) Inventor: Michael A. Creaturo, Siesta Key, FL (US)

(73) Assignee: Parenteral Technologies, LLC, Sarasota, FL (US)

( * ) Notice: Subject to any disclaimer, the term of this patent is extended or adjusted under 35 U.S.C. 154(b) by 397 days.

This patent is subject to a terminal disclaimer.

(21) Appl. No.: 16/205,729

(22) Filed: Nov. 30, 2018

(65) Prior Publication Data

US 2019/0105229 A1 Apr. 11, 2019

Related U.S. Application Data

(63) Continuation of application No. 15/255,725, filed on Sep. 2, 2016, now Pat. No. 10,143,622, which is a (Continued)

(51) Int. Cl.
*A61J 1/10* (2006.01)
*A61J 1/18* (2006.01)
(Continued)

(52) U.S. Cl.
CPC . *A61J 1/18* (2013.01); *A61J 1/10* (2013.01); *A61J 1/1412* (2013.01); *A61J 1/201* (2015.05); *A61J 1/2031* (2015.05); *A61J 1/2062* (2015.05); *A61J 1/2065* (2015.05); *A61J 1/2089* (2013.01); *A61J 1/2096* (2013.01); *A61M 5/1409* (2013.01); *A61M 5/2448* (2013.01); *A61M 5/284* (2013.01); *A61M 5/31596* (2013.01); *A61J 1/2093* (2013.01);
(Continued)

(58) Field of Classification Search
CPC .... A61J 1/10; A61J 1/1412; A61J 1/18; A61J 1/201; A61J 1/2031; A61J 1/2062; A61J 1/2065; A61J 1/2089; A61J 1/2093; A61J 1/2096; A61J 2200/74; A61M 2005/1787; A61M 2005/31598; A61M 5/1409; A61M 5/2448; A61M 5/284; A61M 5/31596
See application file for complete search history.

(56) References Cited

FOREIGN PATENT DOCUMENTS

WO   WO-2010122872 A1 * 10/2010 ........ A61M 5/31596

* cited by examiner

*Primary Examiner* — Kai H Weng
(74) *Attorney, Agent, or Firm* — Suiter Swantz pc llo

(57) ABSTRACT

An infusion apparatus including a body having an infusion reservoir and one end of the body adapted to receive a pierceable end of a vial, a barrel rotatably disposed in an opposing end of the body and having an internal fluid chamber, and a plunger received in one end of the barrel, wherein the barrel rotates relative to the body between a first position allowing bi-directional fluid flow between the barrel and the vial, and a second position allowing bi-directional fluid flow between the barrel and the infusion reservoir, and wherein the plunger is movable relative to the barrel to control the bi-directional fluid flow between the barrel and the vial and the bi-directional fluid flow between the barrel and the infusion reservoir.

13 Claims, 11 Drawing Sheets

Related U.S. Application Data continuation of application No. 14/059,070, filed on Oct. 21, 2013, now Pat. No. 9,433,726.

(60) Provisional application No. 61/716,737, filed on Oct. 22, 2012.

(51) Int. Cl.
| | |
|---|---|
| *A61M 5/14* | (2006.01) |
| *A61J 1/20* | (2006.01) |
| *A61M 5/24* | (2006.01) |
| *A61M 5/28* | (2006.01) |
| *A61M 5/315* | (2006.01) |
| *A61J 1/14* | (2006.01) |
| *A61M 5/178* | (2006.01) |

(52) U.S. Cl.
CPC ... *A61J 2200/74* (2013.01); *A61M 2005/1787* (2013.01); *A61M 2005/31598* (2013.01)

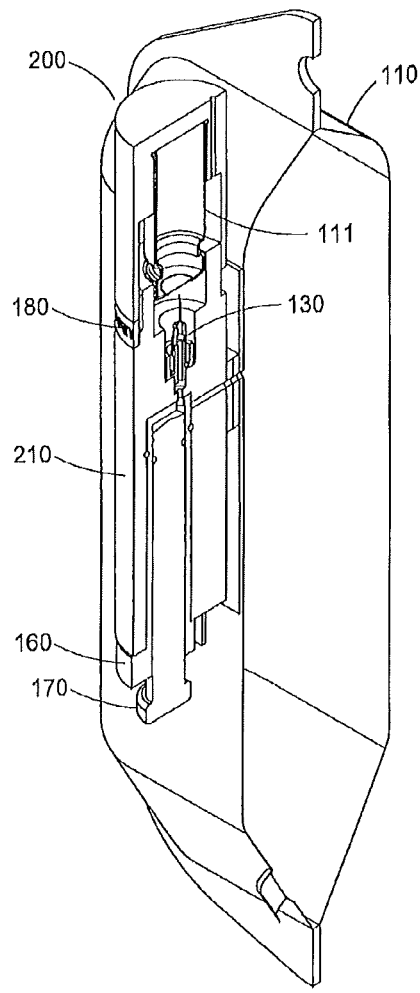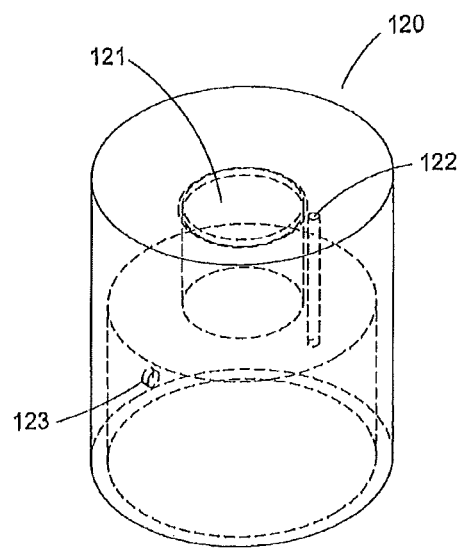
FIG. 3
FIG. 2B

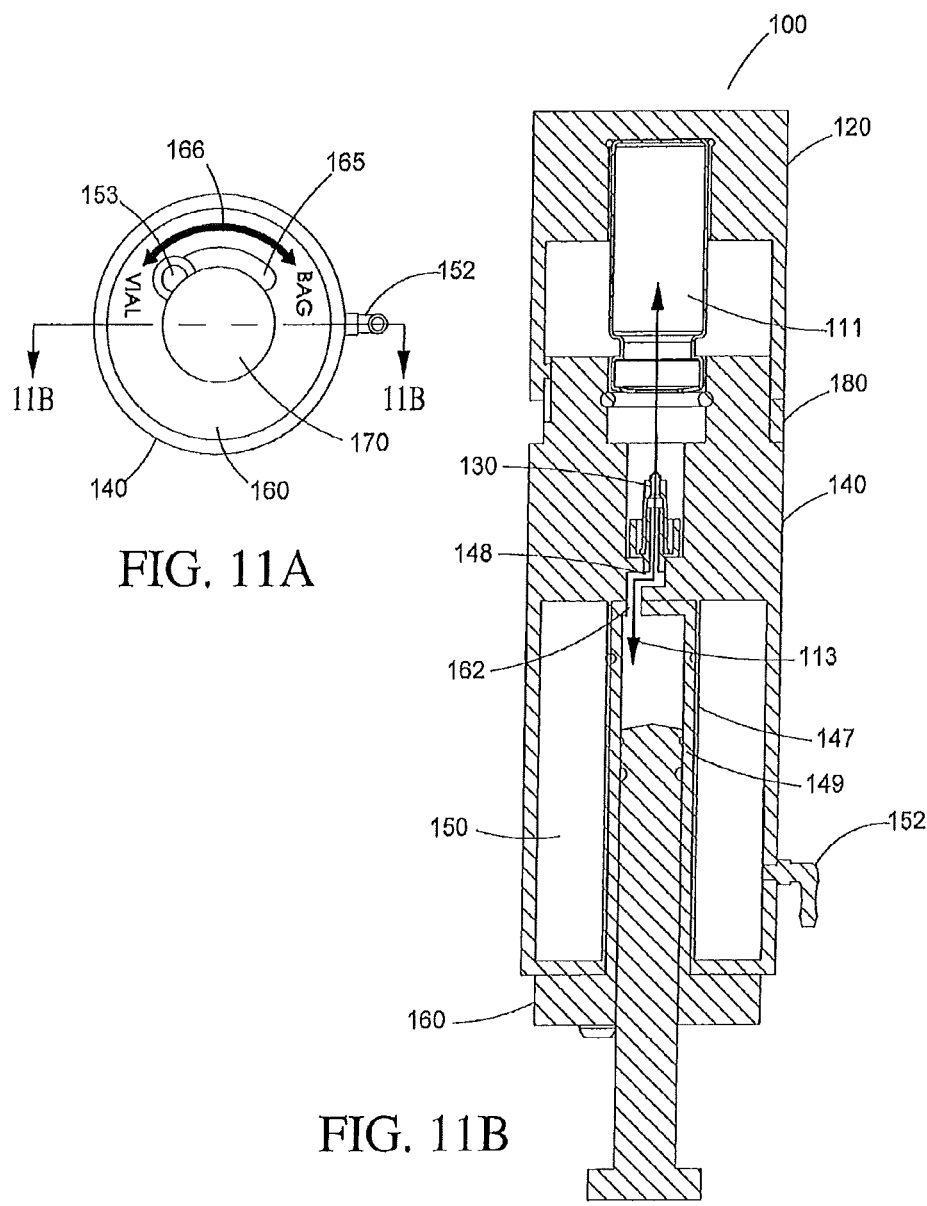

METHODS AND APPARATUSES FOR DELIVERING MEDICAMENTS TO INTRAVENOUS FLUID

CROSS-REFERENCE TO RELATED APPLICATIONS

This application is a continuation of U.S. application Ser. No. 15/255,725 filed Sep. 2, 2016 (now U.S. Pat. No. 10,143,622), which claims priority from U.S. application Ser. No. 14/059,070 filed Oct. 21, 2013 (now U.S. Pat. No. 9,433,726), which claims priority from U.S. Application No. 61/716,737 filed Oct. 22, 2012, the entirety of which are incorporated by reference herein.

TECHNICAL FIELD AND BACKGROUND OF THE INVENTION

The present invention is related, generally, to the field of medicine delivery apparatuses, systems and methods. More specifically, embodiments of the present invention are related to articles, systems, and methods that are used in the preparation and administration of intravenous ("IV") medications to patients, via IV devices, particularly via an IV Bag Container. Through its one piece self-contained design, the invention significantly prevents or completely eliminates three major health and safety issues plaguing the health care industry in connection with the preparation and administration of IV solutions containing medication: sharps injuries, medically administered errors ("MAE's"), and exposure to hazardous medications by the health care professional.

Additionally, the designs of the invention allow a user to control the reconstitution of a medication and also control in metered dosage the medication to be introduced to an IV device solution without the use of any other component or apparatus.

The World Health Organization has estimated the global disease burden from contaminated sharps injuries suffered by health-care workers at the workplace by analyzing 25 risk factors that covered occupation, environment, lifestyle, diet, health practices and substance abuse (WHO, 2002). In this study, only percutaneous exposures (i.e., sharps injuries) were considered because such exposures were associated with the highest risk of transmission and they accounted for the largest proportion of reported exposures. In Canada, Italy, Spain and the United States of America, for example, percutaneous exposures accounted for 66%-95% of all occupational exposures to blood borne pathogens and, of these, needle-stick injuries accounted for 62%-91% (Romea et al., 1995; EPINet, 1998; NaSH, 1999; CCOHS, 2000; Puro et al., 2001). It is estimated that 600,000 to 800,000 needlestick injuries occur per year. These injuries occur from the time the syringe and needle is prepared through its disposal.

There have been numerous reports analyzing the exposure of medical and non-medical staff to hazardous medications. Health Care Professionals and other non-medical staff have numerous opportunities to come in contact with hazardous drugs. Contact can occur during preparation, administration or waste disposal. Accidental injection, inhalation and dermal contact are the primary contributors of exposure to hazardous drugs. Exposure to these drugs has been associated with acute and short term reactions as well as long-term effects. Case reports include skin-related and ocular effects as well as flu-like symptoms and headache. Reproductive studies on health care workers have shown an increase in fetal abnormalities, fetal loss, and fertility impairment. There has also been some indication of increased cases of cancer in healthcare workers exposed to hazardous medications (American Society of Health System Pharmacists. See ASHP guidelines on handling hazardous drugs (Am. J. Health-Syst. Pharm. 2006; 63:1172-93).

Additional studies highlight the critical importance of properly reconstituting a medication and, as such, the manufacturers PI (packet insert) and approved method for the reconstitution should not be altered. For instance, most lyophilized medications require exact measurements of a specific diluent, and some manufacturers require the reconstitution to take place over a period of time to avoid a variety of issues including, incomplete reconstitution, foaming among others. Current commercialized single unit IV bag devices that allow for the transfer of a medication from a Vial to a IV bag offer limited or no control for the reconstitution of a medication.

The disclosed invention allows for an exact amount of diluent to be introduced one or more times and/or over a period of time into the Vial according to manufacturer's approved method to obtain a properly reconstituted solution of the medication.

Furthermore, the disclosed invention allows for the properly reconstituted medication to be controlled during the introduction of the medication to the IV bag's solution by specific metered doses pursuant to the manufacturers' and/or other patient or medication characteristic or demand. This controlled dosing may take place during the preparation and/or during the administration period allowing accurate dosing and/or adjustments for increased strengths of the solution. Current known commercialized products do not allow for controlled reconstitution or metered dosage of the medication.

BRIEF SUMMARY OF THE INVENTION

According to one aspect, the present disclosure is directed to an apparatus for preparing intravenous fluid comprising a container comprising a plurality of chambers in communication with one another, with chambers in controllable communication with one another, and with a first chamber able to be connected to a medicament container comprising a predetermined amount of medicament, and a second chamber comprising a solution. The apparatus operates as an integrated system, said first chamber able to receive solution from a second chamber or other chamber and delivering and receiving a predetermined measured amount of the solution, in a controlled measured flow, to the medicament, and delivering the medicament solution in a predetermined measured amount to the second chamber, with the second chamber delivering and receiving a predetermined measured amount of solution in a controlled measured flow. The solution in the second chamber is preferably a medicament, a diluent, a solution used with injectable medicaments, and combinations thereof.

The chambers are in controllable communication with one another, to achieve a controlled measured flow of their contents, and at least one chamber contains a predetermined amount of medicament, diluent or other solution used in connection with injectable medicaments as would be understood by those skilled in the field. The apparatus operates as an integrated system with no exposure of sharps outside of the apparatus, or need for any further components or devices. In a further aspect, the apparatus comprises an intravenous fluid container in communication with the medicament container. In a further aspect, the medicament container is introduced through various mechanisms to the integrated apparatus to form a single housing.

Preferably, the medicament container is selected from the group consisting of: a vial, ampoule, or other container to hold an injectable medicinal solution or medicinal powder or lyophilized compound, or suspension, etc.

According to a further aspect, the first and second chambers comprise openings, and the openings can align to allow fluid to flow, preferably bi-directionally, from one chamber into another chamber. Preferably, one chamber is rotated relative to another chamber to effect the alignment of the openings in the chambers. Preferably, the apparatus comprises at least one tamper-resistant mechanism, and the fluid from the first chamber is controlled by an apparatus to a predetermined measured amount for the reconstitution or other compounding of a medicament. Preferably, the medicinal solution is then transferred to the second chamber where the reconstituted or compounded medicament solution may be stored for the subsequent infusion.

In addition, the first and second chambers comprise openings, and the openings can align to allow fluid to flow, preferably bi-directionally, from one chamber into another chamber. Preferably, one chamber is rotated relative to another chamber to effect the alignment of the openings in the chambers. Preferably, the apparatus comprises at least one tamper-resistant mechanism, and a release of fluid from at least one of the first and second chambers provides a controlled, predetermined, and metered reconstitution or compounding of a medicament, and the container may be stored for infusion, before or after such reconstitution or compounding.

According to a further aspect, the apparatus further comprises a chamber of intravenous solution in communication with a pre-loaded medicament container in an integrated system such that no sharps are exposed outside of the apparatuses. In a further aspect, the medicament containers are pre-loaded within the apparatus and correlated to the intravenous solution chamber.

In a further aspect, in the apparatus, a first chamber comprises a first container comprising a first liquid and a second chamber comprises a second container comprising a material to be combined with the first liquid, with the fluids combining in the second container. The chambers are preferably dimensioned to accommodate an integrated flow control mechanism that may be pre-filled or ready-to-fill. Preferably, the second container comprises a device used to transfer medication to an intravenous device, and at least one of the first and second chambers comprises a device able to regulate and transfer predetermined volumetric flow into and out of said chambers. The container comprises a device able to regulate and transfer predetermined volumetric flow, preferably bi-directionally, into and out of container. In a preferred aspect, the container is a both a medicinal infusion storage and administration apparatus.

Still further the present disclosure is directed to a method of preparing intravenous fluid comprising the steps of providing a medicament container comprising a plurality of chambers in communication with one another, with the chambers in controllable communication with one another. A first chamber comprises a predetermined amount of a medicament, and a second chamber comprises a predetermined amount of solution, with the first chamber delivering and receiving a predetermined amount of medicament, and the second chamber delivering and receiving a predetermined amount of solution. A first liquid is transferred from one chamber into another chamber to create a reconstituted, or further compounded, medicament and the medicament solution is transferred into an intravenous container without exposing a sharp outside of the medicament container.

Still further, the first chamber, second chamber and intravenous container are integrated into a single apparatus. The liquids used in the first and second chambers are medications, diluents, liquids used in a medical solutions, and combinations thereof. At least one of the first and second chambers comprises a device able to regulate a predetermined and metered volumetric flow into and out of the chambers and in and out of the container. One of more of the chambers is preferably dimensioned to accommodate a pre-filled flow control device. Each chamber preferably comprises an opening, and the openings in each of the first and second chambers are aligned to allow fluid to flow bi-directionally from one chamber into another chamber.

According to a still further aspect, the present disclosure is directed to a kit for administering intravenous fluid. The kit comprises a medicament container comprising a plurality of chambers in communication with one another, with a first chamber comprising a predetermined amount of medicament, and a second chamber comprising a solution, with the first chamber delivering and receiving a predetermined amount of medicament, and said second chamber delivering and receiving a predetermined amount of solution, and an intravenous container in communication with the medicament container, with no sharp is exposed outside of the medicament container. A predetermined dosage is thereby delivered from the medicament container to the intravenous container.

Embodiments of the present invention are directed to a new and improved intravenous solution bag or container, herein referred to as the ("IV Preparation and Administration System"), or other apparatuses for the administration of intravenous medications, designed to increase and facilitate dosing, prevent MAE's and prevent sharp injuries, as well substantially, if not totally, prevent the exposure of the health care professional to hazardous medications when they administer such medications to patients.

More particularly, further embodiments of the present invention are directed to an apparatus and process for withdrawing a preselected, controlled, metered or desired amount of diluent or other solution associated with medicament reconstitution from a solution within the IV Preparation and Administration System and introducing it into a medicament container to reconstitute or further compound a medication, subsequently extracting the medicinal solution to a preselected, controlled, metered volume, dosage, patient weight and/or desired dosage to introducing the desired volume of medication to the IV Preparation and Administration System intravenous solution through an industry acceptable transfer solely through the components and design of the IV Preparation and Administration System with no other apparatuses or components required, thus eliminating multiple hands-on procedures, syringes and needles and additional components to accomplish the same transfer as by currently known solutions.

In other embodiments, the IV Preparation and Administration System may be pre-loaded with a vial of medication that is secured within it by multiple tamper-resistant mechanisms that would prohibit the Vial from being removed or altered in anyway than as originally loaded. The solution in the IV Preparation and Administration System would be pre-determined and correlated for the medication it is pre-loaded with. A user would only need to remove a safety mechanism and depress the Cap down to engage the Vial to the IV Preparation and Administration System for the transfer.

In one embodiment, the present invention's design eliminates the need for a syringe with needle or any other components to transfer injectable medication from a vial, or other container, to an IV Preparation and Administration System's preloaded solution reservoir. The elimination of these components and procedures will prevent many sources of human error and sharp injuries by eliminating the need for users to handle the medication, measure it, and load and/or inject it into to the IV Preparation and Administration System.

More particularly, further embodiments of the present invention are directed to a process for extracting a hazardous medication from a vial or container and then subsequently introducing it into an IV Preparation and Administration System's pre-loaded solution through a closed system transfer solely through the elements and design of the integrated IV Preparation and Administration System, thus eliminating multiple hands-on procedures and additional components to accomplish the same transfer by prior art.

Still further embodiments of the present invention are directed to a pre-packaged tamper-resistant kit containing a specific amount of medication contained within a vial or container consolidated with the IV Preparation and Administration System containing the correct correlating solution for the medication and subsequent IV administration, thus eliminating the need for users to perform calculations, correlate, re-verify, or consolidate components to prepare the medication.

Further embodiments of the present invention relate to apparatuses and systems for the packaging, combining and consolidating of the correct correlating articles for the creation of a ready-to-use injectable IV infusion kit and methods for substantially eliminating medicine administration errors. The combination of the correct components, within a tamper resistant package, substantially prevents or significantly reduces medically administered errors ("MAE's") during the administration of injectable medications to patients.

BRIEF DESCRIPTION OF THE DRAWINGS

The accompanying Figures illustrate aspects of embodiments of the present invention. These, together with the description illustrate the objects, advantages and principles of embodiments of the present invention. In the Figures:

FIGS. 2A and 2B illustrate views of the iV Preparation and Administration System connected to an external IV Bag;

FIG. 3 illustrates a transparent isometric view of the sleeve cap;

FIGS. 11A and 11B illustrate a bottom view (11A) of the flow control barrel dial and cross section view (11B) of the IV Preparation and Administration System with an integrated solution reservoir.

DETAILED DESCRIPTION OF THE INVENTION

Figures 1A, 1B:
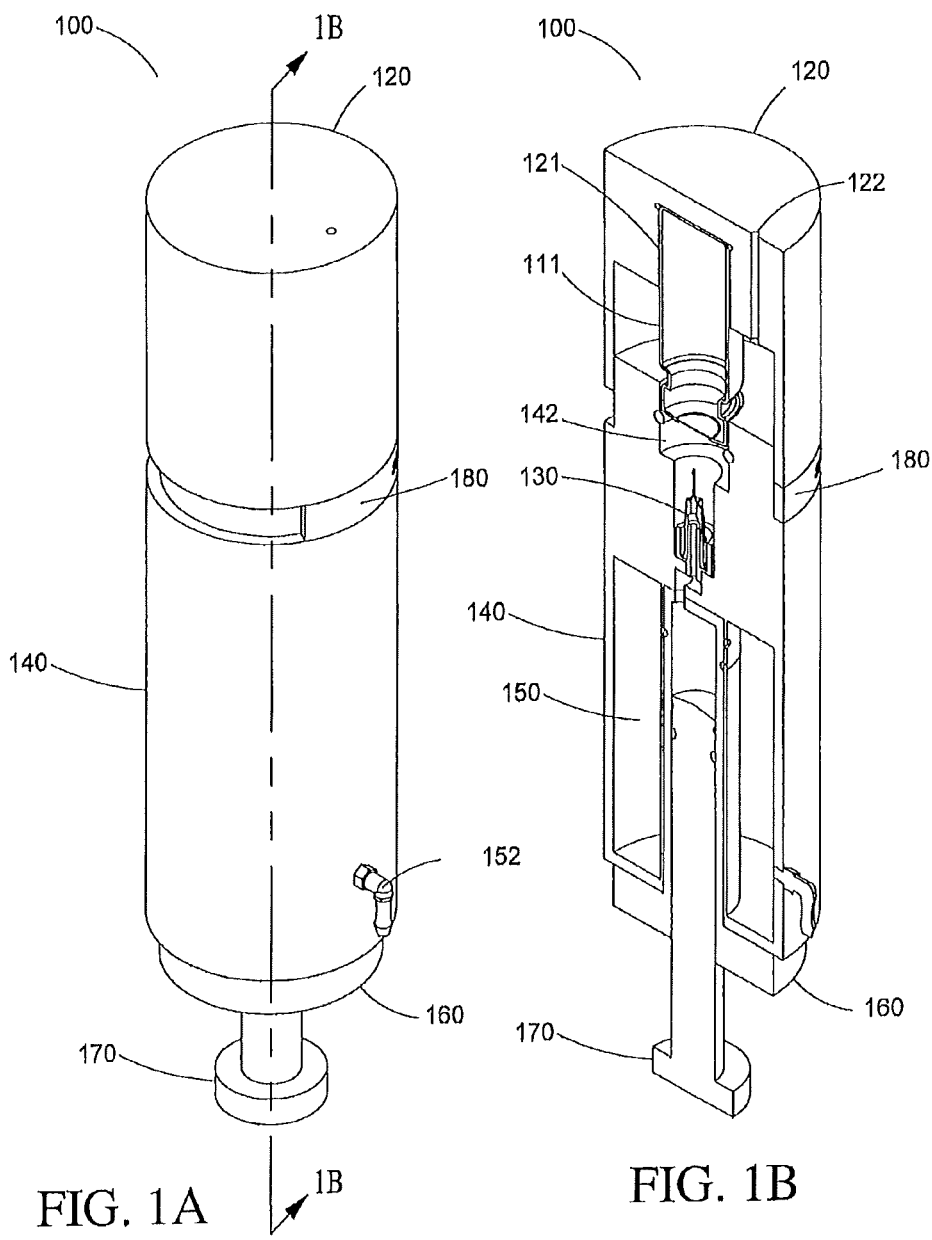
FIGS. 1A and 1B illustrate an isometric view (1A) and cross section (1B) of the IV Preparation and Administration System.

FIGS. 1A and 1B illustrate an isometric view and cross section of the IV Preparation and Administration System 100 with an integrated solution reservoir 150. It is comprised of a sleeve cap 120, piercing and transfer device 130, body with an integrated fluid reservoir 140, flow control barrel and dial 160, plunger 170 and a safety clip 180.

Figure 2A:
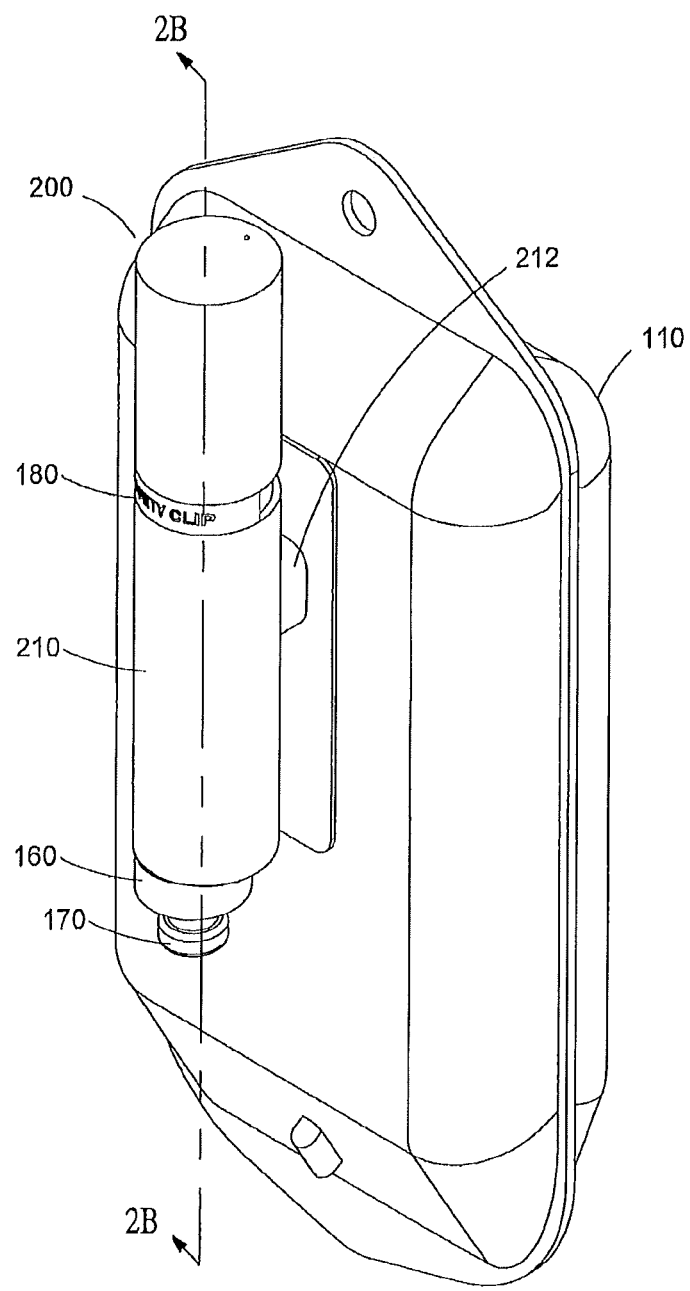

FIGS. 2A and 2B illustrate an isometric view and cross section of the IV Preparation and Administration System 200 for use with an IV Bag 110. It is comprised of a sleeve cap 120, piercing and transfer device 130, body 210, flow control barrel dial 160, plunger 170 and a safety clip 180.

FIG. 3 illustrates a transparent isometric view of the sleeve cap 120 which contains a retainer 121 or other type of holding mechanism that secures a vial 111 in place and provides alignment for penetration by a hypodermic needle, spike, sharp, or other puncture or piercing and material transfer device 130. The sleeve cap 120 has a pressure relief port 122 that allows excess air to release and a tab, nub, clip or other extruding mechanism 123 used to align the sleeve cap 120 and to secure it in place.

Figure 4:
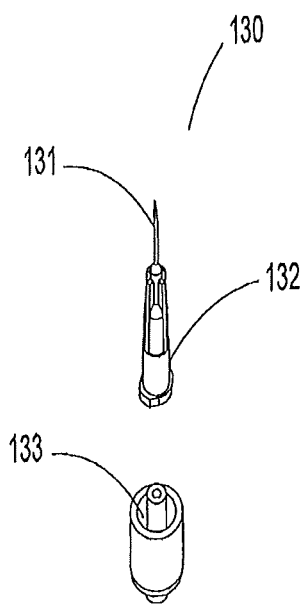
FIG. 4 illustrates a view of the piercing and transfer connection device.

FIG. 4 illustrates an isometric view of the piercing and transfer device 130 is used for the puncturing and engaging of a vial for the transfer of medication and fluid between a vial and the flow control barrel dial 160. The piercing and transfer device 130 will be comprised of a hypodermic needle, spike, sharp, or other puncturing or piercing mechanism 131 that has a female luer lock fitting 132 or other type of interlinking mechanism and a male luer lock fitting 133 or other type of interlinking mechanism.

Figures 5A, 5B:
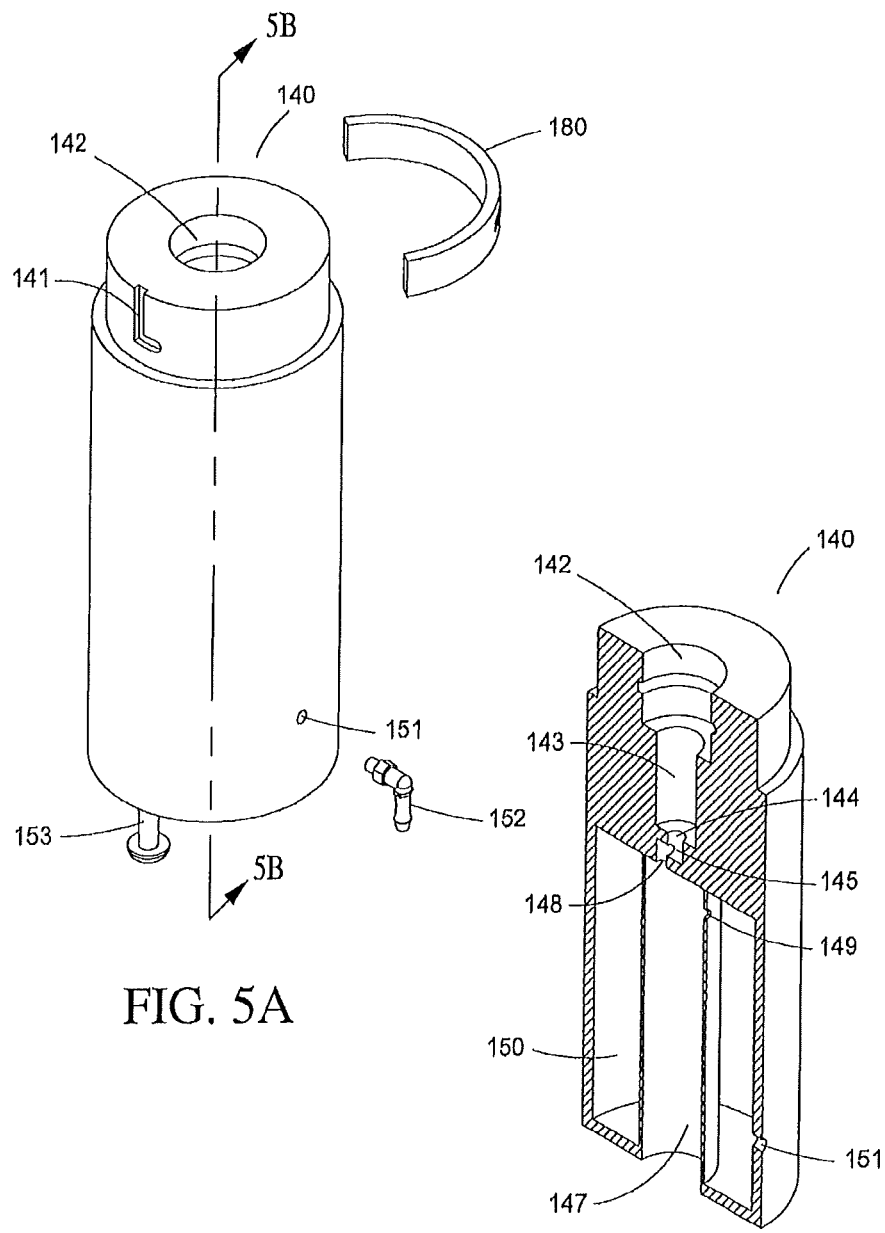
FIGS. 5A and 5B illustrate an isometric view (5A) and cross section (5B) of the body of the IV Preparation and Administration System.

FIGS. 5A and 5B illustrate an isometric view and cross section of the body of the IV Preparation and Administration System 100 with an integrated fluid reservoir 150 which features a safety clip 180 or other apparatus that prevents the sleeve cap 120 from being pushed down and thus engaging the vial 111 to the piercing and transfer device 130. It has a groove, slot or track 141 whereby the sleeve cap's 120 extruding mechanism 123 would align and guide the sleeve cap 120 during loading as well providing a locking mechanism to prevent the sleeve cap 120 from being disengaged. There is an engaging channel 142 which houses and secures the piercing and transfer device 130 and also acts as a guide for the vial 111. The engaging channel 142 has a fitting section 143 where the male luer lock fitting 143 secures into place and aligns with a barrel orifice 144 and channel 145 that leads to an inner barrel 147. The inner barrel 147 provides a channel for insertion of the flow control barrel dial 160, it has a channel orifice 148 that allows bi-directional fluid flow between the flow control barrel dial 160 and a vial 111 and an inner barrel orifice 149 that allows bi-directional fluid flow between the flow control barrel dial 160 and integrated fluid reservoir 150. The body with integrated fluid reservoir 140 also has an external orifice 151 located at the bottom of the integrated fluid reservoir 150 to allow fluid to flow out through an external fitting 152 to tubing or other passage way to withdraw or extract the fluid. A stopper 153 secured to the bottom limits the rotation of the flow control barrel dial 160 within the inner barrel 147.

Figures 6A, 6B:
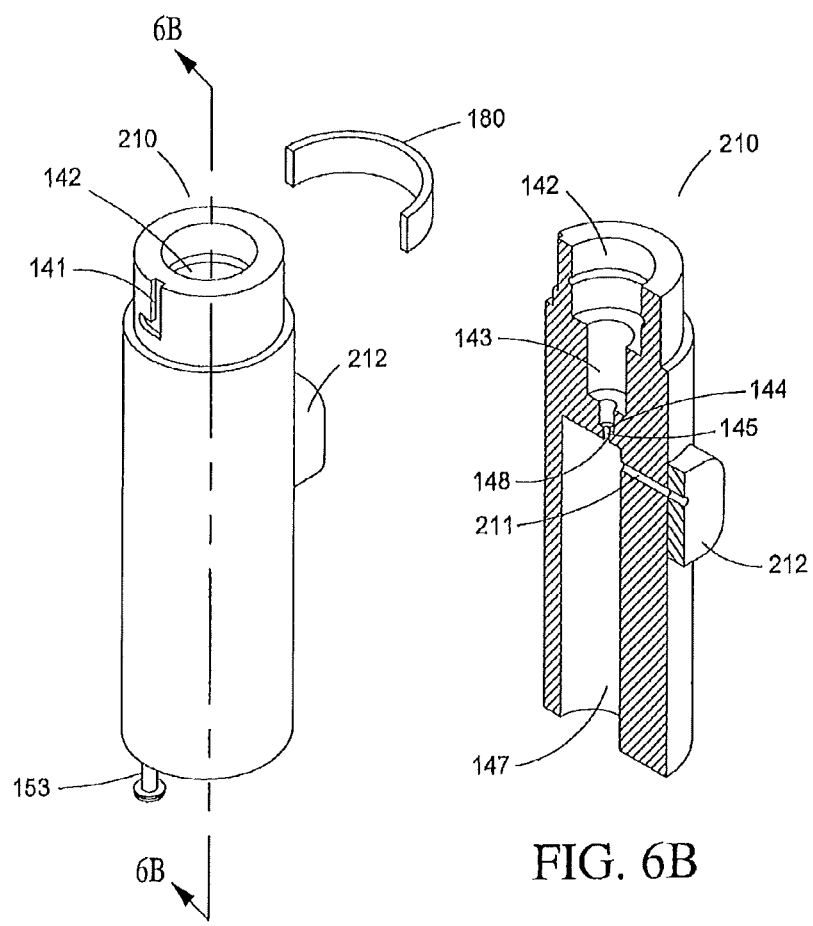
FIGS. 6A and 6B illustrate an isometric view (6A) and cross section (6B) of a groove, slot or track.

FIGS. 6A and 6B illustrate an isometric view and cross section of the body 210 which features a safety clip 180 or other apparatus that prevents the sleeve cap 120 from being pushed down and thus engaging the vial 111 to the piercing and transfer device 130. It has a groove, slot or track 141 whereby the sleeve cap's 120 extruding mechanism 123 would align and guide the sleeve cap 120 during loading as well providing a locking mechanism to prevent the sleeve cap 120 from being disengaged. There is an engaging channel 142 which houses and secures the piercing and transfer device 130 and also acts as a guide for the vial 111. The engaging channel 142 has a fitting section 143 where the male luer lock fitting 143 secures into place and aligns with a barrel orifice 144 and channel 145 that leads to an inner barrel 147. The inner barrel 147 provides a channel for insertion of the flow control barrel dial 160, it has a channel orifice 148 that allows bi-directional fluid flow between the flow control barrel dial 160 and a vial 111 and a IV bag orifice 211 that allows bi-directional fluid flow between the flow control barrel dial 160 and an IV Bag 110. There is an in-line adapter 212 that allows for the connection to an IV Bag 110. A stopper 153 secured to the bottom limits the rotation of the flow control barrel dial 160 within the inner barrel 147.

Figure 7:
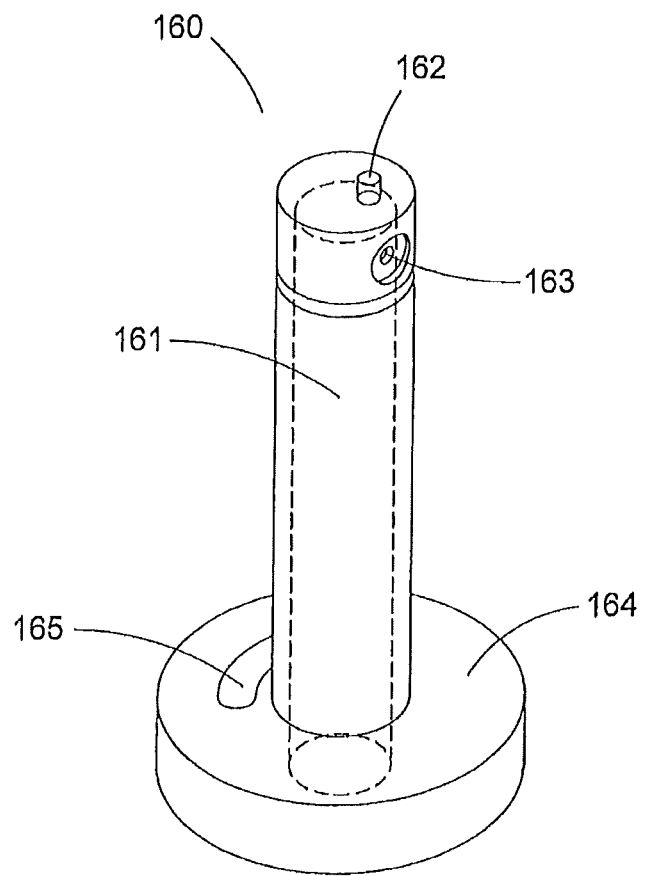
FIG. 7 illustrates a transparent isometric view of the flow control barrel dial.

FIG. 7 illustrates a transparent isometric view of the flow control barrel dial 160 which has a plunger barrel 161, a vial orifice 162, a reservoir orifice 163, a control dial 164 with flow controller 165 and flow directional markings 166.

The vial orifice 162 when aligned with the channel orifice 148 allows for bi-directional fluid flow between the plunger barrel 161 and a vial 111. The reservoir orifice 163 allows for bi-directional fluid flow between the plunger barrel 161 and integrated fluid reservoir 150. The control dial 164 facilitates the rotation of the flow control barrel dial 160 within the inner barrel 147 in order to control the flow of fluid from the plunger barrel 161 to and from a vial 111 or to and from the integrated fluid reservoir 150.

Figure 8:
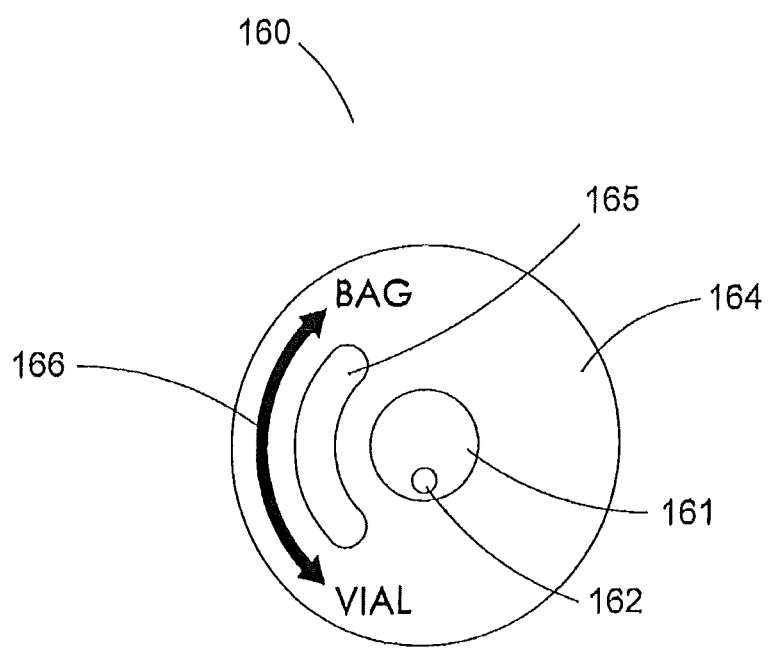
FIG. 8 illustrates a bottom view of the flow control barrel dial.

FIG. 8 illustrates a bottom view of the flow control barrel dial 160. The flow controller 165 guides and restricts the rotation of the flow control barrel dial 160 to allow for perfect alignment of orifices and the flow directional markings 166 designate the direction to turn control dial 164 for transferring fluid to and from a vial 111 or to and from an integrated fluid reservoir 150.

Figure 9:
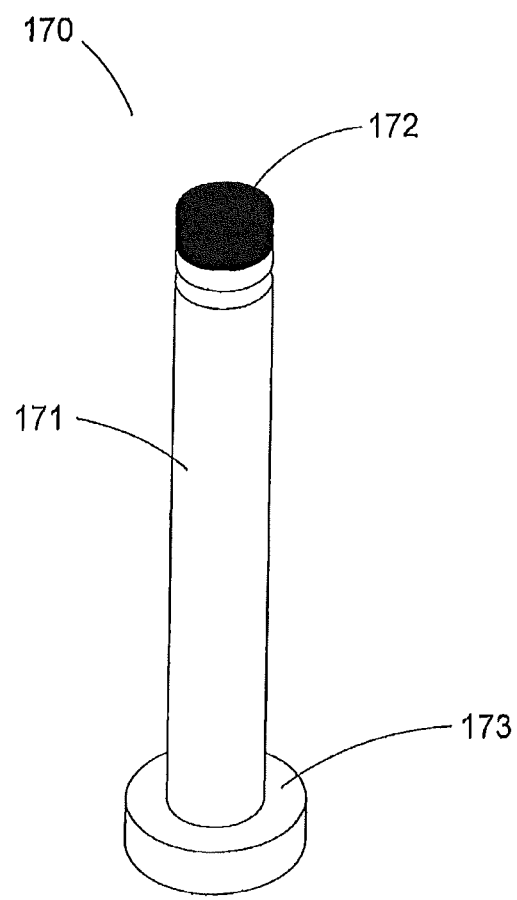
FIG. 9 illustrates a view of the plunger.

FIG. 9 illustrates an isometric view of a plunger 170 which is comprised of a plunger body 171, a rubber gasket tip 172 and a finger knob grip 173.

Figures 10A, 10B:
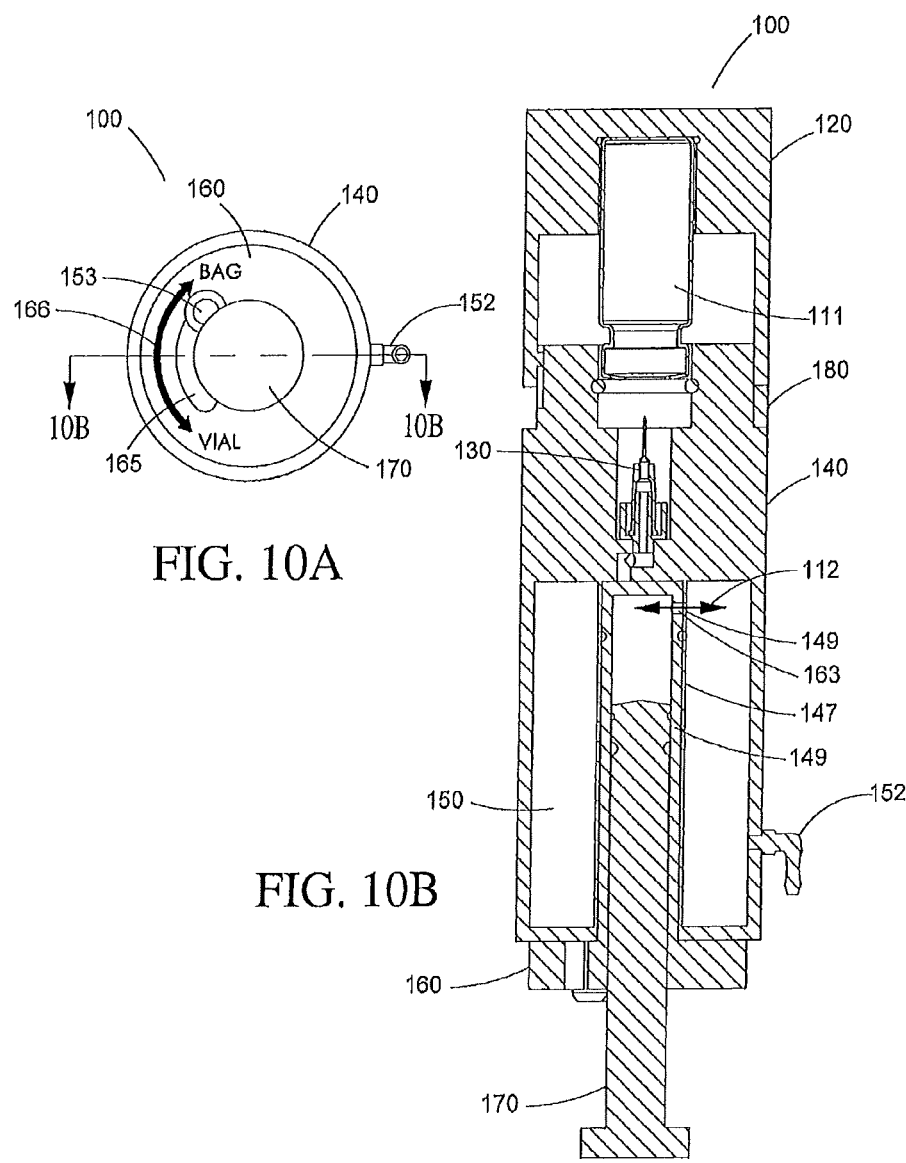
FIGS. 10A and 10B illustrate a bottom view (10A) and cross section view (10B) of the IV Preparation and Administration System.

FIGS. 10A and 10B illustrate a bottom view (10A) of the flow control barrel dial and cross section view (10B) of the IV Preparation and Administration System 100 with an integrated solution reservoir 150 with the flow control barrel dial 160 in the "BAG" position. In this position the reservoir orifice 163 of the flow control barrel dial 160 is aligned with the inner barrel orifice 149 of the body with integrated fluid reservoir 140 to allow bi-directional fluid flow between the plunger barrel 161 and integrated fluid reservoir 150 or IV bag 110 as indicated by a bidirectional arrow 112.

FIGS. 11A and 11B illustrate a bottom view (11A) of the flow control barrel dial and cross section view (11B) of the IV Preparation and Administration System with an integrated solution reservoir 100 with the flow control barrel dial 160 in the "VIAL" position. In this position the vial orifice 162 of the flow control barrel dial 160 is aligned with the channel orifice 148 of the body with integrated fluid reservoir 140 to allow bi-directional fluid flow between the plunger barrel 161 and a vial 111 as indicated by a bidirectional arrow 113.

According to one embodiment, the present disclosure is directed to a process for extracting an injectable medication or other composition from a vial 111 or container (herein referred to as a "Vial") and then introducing it into the IV bag's solution of diluent reservoir 150 (herein referred to as a "Reservoir") through an integrated, closed system transfer, thereby preventing patients and medical professionals from being exposed to hazardous medications, solely through the elements and design of the IV Preparation and Administration System 100 and requiring no other components to conclude this operation. Use of the term "closed", as in a "closed" system, does not necessarily mean that apparatuses of the present disclosure are in fact "closed" via a factory seal. Such a design may be useful where the apparatus is pre-loaded with medicament and "sealed" to reduce chances of tampering or to otherwise insure a sterile, safe transfer and storage of medicine. However, contemplated apparatuses may be opened and loaded with standard vials, ampoules, etc. containing medicaments, into the medicament chamber. The apparatus is then "closed" securely as medicament is drawn into the second chamber housing the diluent or other injectable solution for medicament reconstitution, dosing, etc., or diluent (or other solution) is directed into the medicament chamber to reconstitute the medicament.

Yet another embodiment is directed to apparatuses, methods, systems and kits that substantially eliminate as many sources of human error as possible in the preparation and administration of an injectable infusion medication by eliminating the users need to perform multiple tasks, such as, for example, research, correlations, confirmations and collection of the specific components and the subsequent re-confirmation that each of the components for the infusion are correct, each of which are known opportunities for the introduction of Medical Administered Error's into the infusion administration regimen.

More particularly, further aspects of the present disclosure are directed to pre-packaged tamper-resistant kit comprising, for a particular patient class, medication or other attribute for the particular infusion, a vial and/or other medication container, preferably containing a pre-filled volume of injectable medicine in combination with the correct correlating volume and type of diluent or other injectable solution used in medicament reconstitution, within the IV Bag for the infusion.

Further aspects, are directed to a preformed IV Preparation and Administration System 140 comprising of a pre-loaded Reservoir 150 of solution, herein referred to as that also incorporates a pre-molded hollow cylindrical barrel 147 that extends through the center of the Reservoir 150 or other adjacent position to the Reservoir 150 that bears a single orifice 149 on its body wall, herein referred to as ("Inner Barrel") 147, creating an open bi-directional fluid flow channel from the Reservoir 150 to the inside of the Inner Barrel 147.

In yet further aspects, Inner Barrel 147 will also have an off-centered single orifice and channel on the top of its barrel 148, that extends through the top wall of the Inner Barrel creating an open bi-directional fluid flow channel from the puncture device 130 and barrel orifice 144 to the inside of the hollow barrel center of the Inner Barrel 147.

In still further aspects, a hypodermic needle, spike, sharp or other puncturing or piercing device, (herein referred to throughout this specification as, "Needle" or "sharp") will be connected via a luer lock or other connection channel 133 (that are designed with hollow channels that allows solution to pass freely through it) creating open bi-directional fluid flow channel 148 between the Needle 131 the hollow barrel center of the Inner Barrel 147.

The Reservoir 150 may be volume-scaled for an individual medication dosage range and/or patient weight range and may also bear an indicia or other indication on the Reservoir 150 or body 140 indicating the volume of solution and/or medication specifically calibrated within it.

According to an aspect of the present disclosure, the IV Preparation and Administration System are designed for use with a multiple medications.

In yet another embodiment, the IV Preparation and Administration Systems of the present disclosure may also be clearly and conspicuously labeled to indicate what specific medication the device is intended to administer (separately or within a kit containing the medication).

In further embodiments, the Inner Barrel 147 would have a yet another barrel that is inserted into its hollow center that is designed to have an exterior diameter slightly smaller than the interior diameter of the Inner Barrel, herein referred to as to ("Flow Control Barrel Dial") 160, allowing a substantially water tight snug fit between the Control Barrel Dial 160 and the Inner Barrel 147, however, still allowing the Control Barrel Dial 160 to be rotated while inserted within.

Still further, Control Barrel Dial 160 has a hollow barrel center and also has an orifice on one side of its barrel body 163, and may be designed to incorporate a gasket or other feature extending around the circumference of its orifice 163, herein referred to as ("Control Barrel Reservoir Orifice").

According to further aspects of the disclosure, Control Barrel Dial 160 will also have an off-centered single orifice on the top of its barrel 162, (herein referred to as "Control Barrel Puncture Orifice") that extends through the top wall of the Control Barrel Dial 160 into the hollow barrel center creating an open bi-directional fluid flow channel from the exterior to the inside of the hollow barrel center of the Control Barrel Dial 160.

In yet further aspects, when Control Barrel Dial 160 is rotated within the Inner Barrel 147 to a specific point where the Control Barrel Puncture Orifice 162 aligns with the off centered orifice 148 of the Inner Barrel 147 an bi-directional fluid flow channel opens 113 from the Needle 131 and Vial 111 if attached, to the hollow barrel center 161 of the Control Barrel Dial 160 establishing solution to pass freely through it.

It is further contemplated that, when Control Barrel Dial 160 is rotated within the Inner Barrel 147 to a specific point where the Control Barrel Reservoir Orifice 163 of the Control Barrel Dial 160 aligns with the inner barrel orifice 149, a bi-directional fluid flow channel opening 112 from the Reservoir to the hollow barrel center 161 of the Control Barrel Dial 160 is established, allowing solution to pass freely through it.

A further embodiment contemplates that, when Control Barrel Dial 160 is rotated completely to the lever stop labeled "To Vial" 166 on the Control Barrel Dial 160, Control Barrel Puncture Orifice 162 aligns with the inner barrel orifice 148 of the Inner Barrel 147, and a bi-directional fluid flow channel 113 opens between the inner barrel of 161 of the Control Barrel Dial 160 and, the Needle 131 and Vial 111, if attached, allow solution to pass freely through it.

Under a further aspect of the disclosure, when Control Barrel Dial 160 is rotated completely to the lever stop labeled "To Bag" 166 on the Control Barrel Dial 160 the Control Barrel Reservoir Orifice 163 is aligned to the inner barrel orifice 149, and a bi-directional fluid flow channel 112 opens between the Reservoir 150 and the inner barrel 161 of the Control Barrel Dial, allowing solution to pass freely through it.

In still further embodiments, the rotation of Control Barrel Dial 160 from one lever stop or rotation to another will close the Control Barrel Reservoir Orifice 163 and open the Control Barrel Puncture Orifice 162, or open the Control Barrel Reservoir Orifice 163 and close the Control Barrel Puncture Orifice 162, both effectively controlling the flow of solution: 1) to and from the Vial 111 and the inner barrel 161 of the Control Barrel Dial 160, or 2) to and from the Reservoir 150 and the inner barrel 161 of the Control Barrel Dial 160. Thus, when one channel is open, the other is closed.

In yet further embodiments, the rotation of Control Barrel Dial 160 to the middle 166 of the two lever stops to the labeled OFF 166 position closes both bi-directional fluid flow channels, 112 and 113.

In further embodiments, Control Barrel Dial 160 inner barrel 161 may have a plunger 170 inserted within its hollow inner barrel 161 that will create volumetric suction and force within the inner barrel 161 of the Control Barrel Dial 160.

Still further, the plunger's 170 volumetric suction and force within the inner barrel 161 of the Control Barrel Dial 160, can facilitate volumetric movement of a solution within the inner barrel 161 of the Control Barrel Dial 160 and through-out the bi-directional fluid flow channels, 112 and 113, provided they are open.

In still further embodiments, the plunger 170 inserted in Control Barrel Dial 160 can be accessed externally, allowing it to be pulled outwards or push inwards into the inner barrel 161 of the Control Barrel Dial 160.

In further embodiments, the Plunger 170, or Control Barrel Dial 160 may bear indicia or other specific measurements for dosage, patient weight, BSA, recommended or maximum patient dosage or other patient and/or medication characteristic to calibrate and control the amount of solution introduced to the Vial 111 or the amount of medication being withdrawn from the Vial and introduced to the Reservoir 150 for the infusion, etc. In yet further embodiments, a stop cock valve or other directional valve could be used in facilitating the directional flow of the solution within the channels by design of the invention.

In yet further embodiments, Control Barrel Dial 160 could be replaced by a syringe with plunger, or other device, facilitating volumetric pressure or suction flow. Such a device could be inserted within, and a stop cock valve or other directional valve could be used in substitution for the Control Barrel Dial 160 rotation within the inner barrel 147 and used to facilitate the directional flow of the solution.

Further, the IV Preparation and Administration System comprise an engaging channel 142 with an interior center designed to secure and guide a Vial or other container to be engaged and/or punctured for the transfer of the medication from the Vial 111 or other container to the Reservoir 150, herein referred to as the ("Engaging Channel") 142.

In yet further aspects, the Engaging Channel 142 comprises a sliding cap 120 that would slide over the top protecting the Vial 111 or other medication container.

Still further, the sliding cap 120 would be unable to be removed or depressed without having the port hole cap 122, plug, or other device removed, thus allowing air flow to pass into the sliding cap 120 due to suction from within the sliding cap 120.

In still further aspects, the sliding cap 120 comprises a safety and tamper-resistant feature that would prevent it from being removed, preferably without the removal of a clip, screw, plug, or strip 180 or other device being disengaged or removed.

In yet further aspects, the underside of the top of the sliding cap 120 comprises a coupler or other molded circular tab or other holding mechanism 121 that would secure the bottom of a Vial or other medication container in place.

Still further, the sliding cap 120 is designed to secure the bottom of a Vial or container in place allowing it to then be inserted, engaged and punctured for the transfer, or inserted and stored within the Engaging Channel 142 to be engaged and/or punctured at a later time.

In yet further embodiments, the design of the sliding cap 120 and Engaging Channel 142 may secure a Vial 111 in a tamper-resistant closed compartment directly above the Needle or puncture device.

Still further, the design of the sliding cap 120 secures a Vial 111 above a Needle, puncture device or other mechanism that would pierce the Vial 111 for the transfer of the medication from the Vial 111, or other container to the IV Preparation and Administration System 100 reservoir 150 when depressed, screwed or by other motion. In addition, the design of the sliding cap 120 positioned over the Engaging Channel 142 during the puncture and/or transfer of the medication from the Vial 111 or other container to the Reservoir 150 would preferably prevent any aerosolization of the medication.

Still further, it is contemplated that the sliding cap comprises at least one locking mechanism 180 and slots 141 preventing accidental engagement (and allowing safe and predictably directed transportation of a pre-loaded IV Preparation and Administration System 100) until the user follows specific procedures to allow the engaging of the Vial 111 or other container.

In further aspects, the puncture of the Vial 111 or other container by a Needle 131, spike, puncture device or other device, etc. facilitates the transfer of the medication and/or solution between the IV Preparation and Administration System 100 Reservoir 150 and a Vial 111 or other container.

Still further, the design of the IV Preparation and Administration System 100, specifically the Engaging Channel 142, prevents needle stick injuries, as the Needle 131 or other sharp is completely insulated the Engaging Channel 142, thereby making it significantly less likely that a needle stick could occur. The Puncture Device, Needle 131 and Engaging Channel 142 components positioned within the Engaging Channel 142 preferably comprise a protective cap 120 preventing contamination, preserving sterility and preventing tampering of the components within it.

In yet further aspects of the disclosure, the IV Preparation and Administration System 100 may be designed to comprise an exterior solution source, such as IV bag 110 or other container 200 in which an in-line adapter 212 would facilitate the bi-directional fluid flow channel 112 between the external IV bag 110 or other source. The inner barrel 161 of the Control Barrel Dial then allows solution to pass freely through it, and allows all other design features to function as described herein.

In yet further aspects, when the IV Preparation and Administration System 100 is utilizing an external reservoir or IV bag 110, the external reservoir would be designed to be use the similar functions as the internal Reservoir IV Preparation and Administration System 100; with the exception of when the Control Barrel Dial 160 is rotated completely to the lever stop labeled "To Bag" 166, the Control Barrel Dial 160 directly aligns the Control Barrel Reservoir Orifice 163 to the external reservoir orifice on the IV bag 110 or other external source, in which a bi-directional fluid flow channel 112 would open between the external source reservoir and the inner barrel 161 of the Control Barrel Dial establishing solution to pass freely through it.

In yet further aspects, the IV Preparation and Administration System 100 may have a pre-loaded compartment containing the medication that can be transferred to the Reservoir 150 through the designs herein described. Such a pre-loaded compartment may replace a Vial or other container used to hold the medication.

In further aspects, the IV Preparation and Administration System 100 may be constructed out of any suitable medical grade polyethylene, acrylic, etc., among others, ensuring the stability of the medication and solution within it, as well preventing the leaching of medications and the plastics.

In a further aspect, the IV Preparation and Administration System 100 could be designed as a one-unit device kit being pre-filled, pre-loaded, and ready to transfer a specific dosage of medication that is correlated to a specific amount of solution required for that particular IV medication, medication's dosage or patient, patient class or other patient and/or medication specific attribute. The IV Preparation and Administration System 100 could be designed as a pre-packaged ready-to-use kit containing Vial 111 with a specific dosage of medication that is correlated to a specific amount of solution required for that particular IV medication or medication's dosage that is already inserted within the Engaging Channel 142, yet not engaged.

In yet a further aspect, the IV Preparation and Administration System 100 could be designed as a pre-packaged ready-to-use kit containing Vial 111 with a specific dosage of medication that is correlated to a specific amount of solution in the Reservoir 150 required for that particular IV medication, medication's dosage or patient, patient class or other patient and/or medication specific attribute that is already inserted within the Engaging Channel 142, yet not engaged, whereby depressing the Sleeve cap, by pushing, rotating, screwing, etc., presses the Vial 111 or other container onto the Needle 131 or other puncture device thus allowing penetration and subsequent transfer as described herein of the medication to the Reservoir.

In further aspects, the in-line adapter 212 connection in the external reservoir comprises other design features such as a check valve or other connections allowing and enhancing an effective aseptic bi-directional fluid flow channel connection 211 between the inner barrel 161 of the Control Barrel Dial 160 and the external container or IV Bag 110.

The following exemplary protocols are set forth as one possible example for using the apparatuses, methods, systems and kits of the present disclosure, and are not meant to represent an exhaustive listing of protocols, but is only presented to help understand aspects of the disclosure.

Liquid Medication Transfer, (not Pre-Loaded in Sleeve)
1) Uncap and or unscrew protective cap and dis-engage all tamper resistant controls.
2) Uncap Needle.
3) Prepare Vial top for the transfer.
4) Place Vial within the engaging channel or Sleeve Cap and re-place protective cap.
5) Push firmly downward on Cap until completely depressed.
6) Turn the flow control barrel dial towards the label "TO VIAL" and the protruding lever stop until the lever cannot go further.
7) Pull out plunger in flow control barrel dial until filled or at appropriate dosage as indicated on the plunger flow or control barrel dial.

8) Turn the flow control barrel dial towards the label "TO Bag" and the protruding stop until the lever cannot go further.

9) Push the Plunger slowly inwards until fully inserted emptying the contents or to the measured dosage or per Indicia as indicated on the flow control barrel dial or plunger into the solution reservoir of IV bag.

Liquid Medication Transfer, (Pre-Loaded in Sleeve)

1) Dis-engage all tamper resistant controls preventing the sliding sleeve cap from engaging.

2) Push sliding Sleeve cap downward until completely depressed.

3) Turn the flow control barrel dial towards the label "TO VIAL" and the protruding lever stop until the lever cannot go further.

4) Pull out plunger in flow control barrel dial until filled or at appropriate dosage as indicated on the plunger or flow control barrel dial.

5) Turn the flow control barrel dial towards the label "TO Bag" and the protruding stop until the lever cannot go further.

6) Push the Plunger slowly inwards until fully inserted emptying the contents or to the measured dosage or per Indicia as indicated on the flow control barrel dial or plunger into the solution reservoir of IV bag.

Reconstitution Powder for Medication Transfer

1) Dis-engage all tamper resistant controls preventing the sliding sleeve cap from engaging.

2) Push sliding Sleeve cap downward until completely depressed.

3) Turn the flow control barrel dial towards the label "TO BAG" and the protruding stop until the dial cannot go further.

4) Pull out plunger from the flow control barrel dial until filled or at appropriate volume as indicated on the plunger or flow control barrel dial.

5) Turn the rotation flow control barrel dial towards the label "TO VIAL" and the protruding stop until the dial cannot go further.

6) Push the plunger within the flow control barrel dial slowly inwards until fully inserted emptying the solution contents of the barrel into the Vial or to the measured dosage is reached as per Indicia on plunger or the flow control barrel dial.

7) After reconstitution of the particular medication based upon manufacturers criteria. Pull out the plunger in within the flow control barrel dial until filled or at appropriate volume and/or dosage as indicated on the plunger or flow control barrel dial.

8) Turn the flow control barrel dial towards the label "TO BAG" and the protruding stop until the lever cannot go further.

9) Push the plunger of the flow control barrel dial slowly inwards emptying the contents of the barrel into the solution reservoir at appropriate dosage or amount as indicated on the plunger or flow control barrel dial.

Reconstitution Powder for Medication Transfer (Not Pre-Loaded)

1) Uncap and or unscrew protective cap and dis-engage all tamper resistant controls.

2) Uncap Needle.

3) Place Vial within the engaging channel or Sleeve Cap and re-place protective cap.

4) Push firmly downward on Cap until completely depressed.

5) Turn the flow control barrel dial towards the label "TO BAG" and the protruding stop until the dial cannot go further.

6) Pull out plunger in flow control barrel dial until filled or at appropriate dosage and/or volume as indicated on the plunger or flow control barrel dial.

7) Turn the flow control barrel dial towards the label "TO VIAL" and the protruding stop until the dial cannot go further.

8) Push the Plunger slowly inwards until fully inserted emptying the solution contents of the barrel into the Vial or to the measured volume or dosage is reach as indicated on the plunger or flow control barrel dial.

9) After reconstitution of the particular medication based upon manufacturers criteria, pull out plunger in flow control barrel dial until filled or at appropriate volume and/or dosage as indicated on the plunger or flow control barrel dial.

10) Turn the flow control barrel dial towards the label "TO BAG" and the protruding stop until the dial cannot go further.

11) Push the plunger slowly inwards emptying the contents of the barrel into the solution reservoir of IV bag until empty or at appropriate dosage as indicated on the plunger or flow control barrel dial.

The preferred liquids according to the disclosure are medications, diluents, or other liquids used to prepare a medicinal solution, or reconstitute a medicament, etc., and one or both of the containers are medicinal storage containers or intravenous containers or other apparatus used to contain, mix, or administer medications. The second container may contain a solid, liquid, gas, or combination thereof that is to be combined with the liquid to be transferred into the second container. The containers used in the device may themselves be devices used to transfer or infuse medication or other substances into a medical patient.

It is further understood that the apparatus of the disclosure contains chambers (for medicaments, diluents, other liquids used to prepare medicinal solutions, etc.) that are dimensioned to receive and hold traditional containers used for such medicaments, diluents, other liquids used in medicinal solutions etc. In another aspect, the chambers are dimensioned to themselves be pre-loaded to hold and retain such medicaments, diluents, etc. without use of traditional medicinal containers such as, for example, vials and/or ampoules, etc.

According to one aspect, at least one container comprises a pre-formed cylindrical hollow column connected to a needle spike, sharp, or other puncture device (collectively referred to herein as a "sharp") that has a hollowed interior center in which a second column or other apparatus within it may predictably regulate volumetric flow and also volumetric suction and/or pressure. The cylindrical hollow column or channel extends from the top of one of the containers where it may be connected to a needle or other puncture device then extend through the container's solution reservoir to the bottom of the container that allows access to a hollowed interior center in which a second column or other apparatus can be inserted within it to predictably regulate or meter volumetric flow and also volumetric suction and/or pressure by means of a plunger or other device within the interior of the second column.

One of the containers may be an intravenous container or other apparatus having a fixed pre-formed hollow column extending from the top of the container where it is connected through a channel to the container's reservoir of solution, then extending through the reservoir itself to the bottom of the container that allows access to its hollowed interior center where a sharp or other puncturing device containing medication can be inserted via luer lock or other connection allowing the medication to be predictably transferred through volumetric suction or pressure into the solution contained in the container. Preferably, each of two hollow cylindrical columns has a hole or other opening at the top of, bottom of and/or on one side of its barrel. The holes are positioned so that the columns can be rotated to align the holes. When the holes are aligned, fluid may flow bi-directionally from one container to the other. Preferably, at least one of the containers contains a preselected amount of solution or diluent in the container and such container also has a preformed cylindrical hollow column or channel connected to the container's reservoir of solution that allows access to its hollowed interior center where a syringe or other device containing medication can be inserted via luer lock or other connection allowing the medication to be transferred into the container's solution and/or contents.

According to a further aspect, one or both containers contains a preselected amount of solution or diluent with the container having a fixed, preformed cylindrical hollow column extending from the top of the container where it is connected through channels to the second container's reservoir solution, then extends through the reservoir itself to the bottom of the second container that allows access to its hollowed interior center where a syringe or other device containing medication can be inserted via luer lock or other connection allowing the medication to be transferred into the second container. The second container is an intravenous container that is used to administer medication to a patient. One column is in communication with another rotated to a certain position whereby the holes and/or openings on the columns would align and thus create a common opening though the columns. The two hollow cylindrical columns with openings in the top of the column and/or on the side of the column may be rotated to a certain position in which the holes and/or openings on the sides of the columns would align and the top holes would not align and vice versa. The two hollow cylindrical columns are used to control the flow of volume to and from (bi-directionally) the intravenous container and the syringe or other apparatus containing medication and vice versa through rotation of the inner column. The inner column may be inserted within a pre-formed fixed column and may be freely rotated within the interior of the fixed column. The column that may be inserted within preferably comprises a lever or other feature that would enable the user to freely circularly rotate the column within the other column. The column that may be inserted within another column may comprise a plunger or other device inserted within its hollow center thus creating volumetric suction or pressure. According to a further aspect, the two columns may bear indicia allowing measured dosages and controlled re-constitution of the solution to and from an intravenous bag and the container holding the medication. Further, the device inserted into the column to create predictable and metered volumetric movement may bear indicia allowing measured dosages and controlled re-constitution to and from the intravenous bag and the apparatus containing the medication. The preformed column may be connected through a luer lock or other connector channels to a needle or other puncture device for the transfer of the medication from the container to the apparatus.

As stated above, apparatuses of the disclosure may comprise a pre-filled syringe, whereby the syringe is inserted into the column and connected it through various means would allow the contents of the syringe to be added to the container's solution.

Further aspects of the disclosure are directed to a pre-packaged kit in which the apparatus containing a medication may be connected at time of administration or may come pre-connected. The apparatus containing the medication may have a plunger or other apparatus to deliver the medication through means of volumetric pressure. The device containing the medication may have an indicia or other calibration allowing for a specific amount of medication to be introduced to the reservoir of the intravenous container. The intravenous container holds a pre-selected amount of medication in a pre-filled container (for example, a syringe, etc.), vial, or other apparatus, and may contain medication within a compartment within the device. Therefore, it is understood that the pre-packed kit may comprise an intravenous container for an injectable infusion containing the correct pre-determined volume of diluent for the particular infusion and a pre-determined volume of medication within a Vial or other container corresponding and correlating to the diluent and to the particular infusion.

According to the present disclosure, the apparatuses, methods, systems and kits reduce errors in the administration of an injectable infusion medicine by consolidating and combining the correct correlating articles and components for a pre-packaged kit for providing the creation of a ready-to-use injectable IV infusion kit and methods, for substantially preventing or significantly reducing medically administered errors ("MAE's") during the administration of injectable medications to patients.

As described above, the Vial or other container containing the medication may be suspended within the Sleeve ready to be engaged. Further, the Vial or container within the Sleeve may also be sealed within the Sleeve by a tamper-resistant cap that prevents, without disabling, the access to the Sleeve and as well the container holding the medication. The tamper-resistant cap is understood to prevent removal of the cap and medicament from the apparatus. Still further, the cap that covers the Sleeve may have a round coupler or other molded device that secures the bottom of the Vial or other container holding the medication, Vial, or container within the Sleeve, and the cap itself may be used to form or create a portion of a containment chamber. The cap may be used to secure the Vial, or other container holding the medication, within a specific position pending engagement for the transfer or during transfer. The cap may be used to further engage the Vial, or other container holding the medication, as the cap is depressing or screwed downwards on the Vial or container, and the cap may be used to prevent the aerosolization and exposure to the medication during the transfer of medication from the Vial or container to the IV Preparation and Administration System solution, or during storage. It is understood that the cap may comprise a pressure relief feature comprising a filter valve, a one-way valve, etc. to release pressure within a containment top. In this way, in this aspect, the cap or top may be a safety cap that facilitates control and actuation of the transfer of the medicament to the apparatus. It is further contemplated that the cap or top is a safety cap having or used in conjunction with a holding mechanism to secure a vial or other medicament container to the cap and/or in proper orientation within a chamber during preparation, loading and storage.

The apparatuses described herein allow for a one-time or repeated controlled and metered reconstitution of the medication contained in a vial or other container, with the solution contained in or transferred to an intravenous bag, and also offers predictably measured dosage of the medication itself from the vial or other container for transfer to the solution contained in the intravenous bag. The plunger, barrel or other apparatus described therein may bear indicia that allow the volume of solution and medication to be transferred based on the volume or mass of the solution or medication, or based on the weight (or body mass) of the patient who will receive the medication. The indicia may also indicate a conversion of the medication dosage strength to patient weight, for recommended, maximum, or other patient dosage schedule for the infusion.

According to the present disclosure, there is no need for any additional components or devices required to complete the medicament reconstitution and transfer of medication from the Vial or other container holding the medication to the apparatus' intravenous solution, or solution from the apparatus to the Vial or container. Further, there is no need for any additional connections, threads or other components necessary to be installed or designed on a vial, for it to be engaged to the apparatus for the proper transfer of the medication. As set forth above, one of the containers may come pre-connected or with a connection for attaching a syringe, hypodermic needle, sharp or other puncture device to facilitate the transfer of the medication and/or solution from a vial or other medicament container to the intravenous solution of the IV Preparation and Administration System.

While the preferred variations and alternatives of the present disclosure have been illustrated and described, it will be appreciated that various changes and substitutions can be made therein without departing from the spirit and scope of the disclosure. Therefore, it is to be understood that the invention is not to be limited to the specific embodiments disclosed and that modifications are intended to be included within the scope of the appended claims. Although specific terms are employed herein, they are used in a generic and descriptive sense only and not for purposes of limitation.

What is claimed is:

1. An infusion apparatus, comprising:
   a body having an infusion reservoir for containing a predetermined volume of fluid, one end of the body including an engaging channel adapted to receive therein a pierceable end of a vial such that the vial is movable toward the body to pierce the pierceable end of the vial;
   a barrel rotatably disposed in an opposing end of the body, the barrel rotatable relative to the body and having an internal fluid chamber; and
   a plunger received in one end of the barrel;
   wherein the barrel rotates relative to the body between a first position allowing bi-directional fluid flow between the barrel and the vial, and a second position allowing bi-directional fluid flow between the barrel and the infusion reservoir; and
   wherein the plunger is movable relative to the barrel to control the bi-directional fluid flow between the barrel and the vial and the bi-directional fluid flow between the barrel and the infusion reservoir.

2. The infusion apparatus of claim 1, wherein the barrel comprises a first opening permitting bi-directional fluid flow between the barrel and the vial when the barrel is in the first position, and a second opening permitting bi-directional fluid flow between the barrel and the infusion reservoir when the barrel is in the second position.

3. The infusion apparatus of claim 1, wherein the barrel is marked with first indicia visible when the barrel is in the first position, and second indicia visible when the barrel is in the second position, the first indicia indicating the fluid and a predetermined volume required for reconstituting a medicament, and the second indicia indicating dosage unit in at least one of volume, mass, potency, patient weight, and patient characteristic.

4. The infusion apparatus of claim 3, wherein the dosage unit is indicated in at least two of volume, mass, potency, patient weight, and patient characteristic.

5. The infusion apparatus of claim 1, further comprising a removable safety clip for preventing movement of a vial toward the body.

6. The infusion apparatus of claim 1, further comprising an outlet through the body for exiting the fluid from the infusion reservoir.

7. The infusion apparatus of claim 6, wherein reconstituted medicament fluid flow through the outlet is independent of the bi-directional fluid flow between the barrel and the vial and the bi-directional fluid flow between the barrel and the infusion reservoir.

8. The infusion apparatus of claim 6, wherein in operation a vial end is engaged in the engaging channel, the vial is moved toward the body to pierce the vial, the barrel is rotated to the second position, the plunger is withdrawn from the barrel to draw the fluid into the barrel, the barrel is rotated to the first position, the plunger is advanced into the barrel to force the fluid into the vial, the plunger is withdrawn from the barrel to draw the reconstituted medicament into the barrel, the barrel is rotated to the second position, and the plunger is advanced into the barrel to force the reconstituted medicament into the infusion reservoir and out the outlet.

9. The infusion apparatus of claim 1, further comprising indicia indicating at least one of medicament name and fluid name.

10. The infusion apparatus of claim 1, further comprising a dial at one end of the barrel configured to engage with the body to lock the barrel in one of the first position, the second position, or a third position in which bi-directional fluid flow is prevented between the vial and the barrel and between the barrel and the infusion reservoir.

11. The infusion apparatus of claim 1, further comprising a vial puncture device disposed between the body and the vial arranged to puncture the vial in response to movement of the vial toward the body or the body toward the vial.

12. The infusion apparatus of claim 1, wherein the fluid is at least one of a diluent, a solution, intravenous fluid, and a liquid.

13. The infusion apparatus of claim 1, wherein when the barrel is in the first position bi-directional fluid flow between the barrel and the infusion reservoir is prevented, and when the barrel is in the second position bi-directional fluid flow between the barrel and the vial is prevented.

* * * * *